United States Patent [19]

Onodera et al.

[11] Patent Number: 5,144,134
[45] Date of Patent: Sep. 1, 1992

[54] METHOD FOR DETERMINING THE QUALITY OF A LUBRICANT LAYER ON A MAGNETIC RECORDING MEDIUM BY DETECTING ELECTRONS AT VARYING DRAWING ANGLES

[75] Inventors: Katsumi Onodera; Youichi Tei, both of Matsumoto, Japan

[73] Assignee: Fuji Electric Co., Ltd., Japan

[21] Appl. No.: 711,168

[22] Filed: Jun. 5, 1991

[30] Foreign Application Priority Data

Jun. 5, 1990 [JP] Japan .................................. 2-146632

[51] Int. Cl.$^5$ .............................................. H01J 37/00
[52] U.S. Cl. .................................. 250/307; 250/305; 250/306; 250/310
[58] Field of Search ............... 250/305, 306, 307, 310, 250/397; 73/64

[56] References Cited

U.S. PATENT DOCUMENTS

| | | | |
|---|---|---|---|
| 4,358,680 | 11/1982 | Read | 250/305 |
| 4,752,685 | 6/1988 | Shiokawa et al. | 250/305 |
| 4,777,364 | 10/1988 | Sartore | 250/307 |
| 4,857,230 | 8/1989 | Pierre | 250/305 |
| 5,055,679 | 10/1991 | Ninomiya et al. | 250/306 |

*Primary Examiner*—Jack I. Berman
*Assistant Examiner*—James Beyer
*Attorney, Agent, or Firm*—Brumbaugh, Graves, Donohue & Raymond

[57] ABSTRACT

The quality of a lubricant layer formed on a surface of a magnetic recording medium is determined by exposing the lubricant molecules of the lubricant layer to a radiation source for x-ray photoelectron spectroscopy while varying the photoelectron drawing angle. The number of emitted electrons is determined and, from this, the degree of orientation and the quality of the lubricant layer is found.

6 Claims, 8 Drawing Sheets

METHOD FOR DETERMINING THE QUALITY OF A LUBRICANT LAYER ON A MAGNETIC RECORDING MEDIUM BY DETECTING ELECTRONS AT VARYING DRAWING ANGLES

BACKGROUND OF THE INVENTION

This invention is concerned with a method of determining the quality of a lubricant layer on a surface of a magnetic recording medium particularly magnetic recording media used as fixed disk auxiliary storage devices for information processing systems. Conventional magnetic recording media of this type typically are formed from a nonmagnetic substrate, a magnetic layer, a protective layer, for example of carbon, and a lubricant layer. The lubricating layer and the protective layer together are intended to provide the environmental resistance, wear resistance and lubricity necessary in a device of this type. It is therefore important that the lubricating layer provide an effective and consistent surface upon which the magnetic recording head can ride. In many cases, however, this is not obtained.

Lubricant layers (particularly fluorocarbon lubricants) formed on a carbon protective layer of a magnetic recording medium may be defective as a result of uneven lubricating properties of the lubricant layer. When such unevenness is present, the friction coefficient of the lubricant layer with respect to a magnetic head is so small that it is difficult to stably obtain a good lubricating property which would minimize the "sticking" of the magnetic head to the recording medium. Heretofore, however, there has been no way to quantitatively test the quality of the lubricant layer short of a long term wear test. It is an object of the present invention to provide such a method.

SUMMARY OF THE INVENTION

It has now been discovered that the quality of a lubricant layer on a surface of a magnetic recording medium can be determined using X-ray photoelectron spectroscopy (ESCA) techniques. This method relies on the understanding that the quality of a lubricating layer is related to the degree of orientation of the lubricant molecules making up the lubricant layer and the fact that this can be quantified by ESCA. Thus, in accordance with a first embodiment of the invention, the lubricant molecules formed on the lubricant layer of the surface of a magnetic recording medium are exposed to a radiation source for ESCA while the photoelectron drawing angle is varied. The number of electrons emitted at various drawing angles is determined and from this the degree of orientation, and hence the quality of the lubricant layer, is found.

DETAILED DESCRIPTION OF THE INVENTION

As used in this application, a lubricant layer refers to a coating of lubricant molecules each comprising a main chain and a polar group portion formed on the surface of a magnetic recording medium. Advantageously, the lubricant molecules are fluorocarbons of the type generally used in the magnetic recording industry.

It is believed that in the case of forming a fluorocarbon lubricant layer on a carbon protective layer, the lubricant is present in various forms depending on the quality and surface roughness of the protective layer, the method of forming the lubricant layer, the treatments (for example, heat treatment) before and after the formation of the lubricant layer and the chemical structure of the lubricant, and on the fact that the lubricating property varies in accordance with the form in which the lubricant is present.

Further, it is generally the case that the larger the molecular weight of the lubricant molecule, and thus the longer its main chain portion, the better the coefficient of friction. On the other hand, lubricant molecules with a lower molecular weight constitute a higher quality lubricant layer, with less sticking of the head, than those with a higher molecular weight. The same is true for lubricant molecules having a polar group at the end of the main chain portion as compared to those without one. From these observations, it appears that if the lubricant layer is composed of lubricant molecules having polar groups oriented toward the protective layer side, improved lubricating properties would result. The method of the invention confirms this expectation. Also, when the lubricating layer is oriented so that the polar groups are toward the protective layer, the adhesion of the lubricant molecules with the protective layer is improved.

Figure 8:
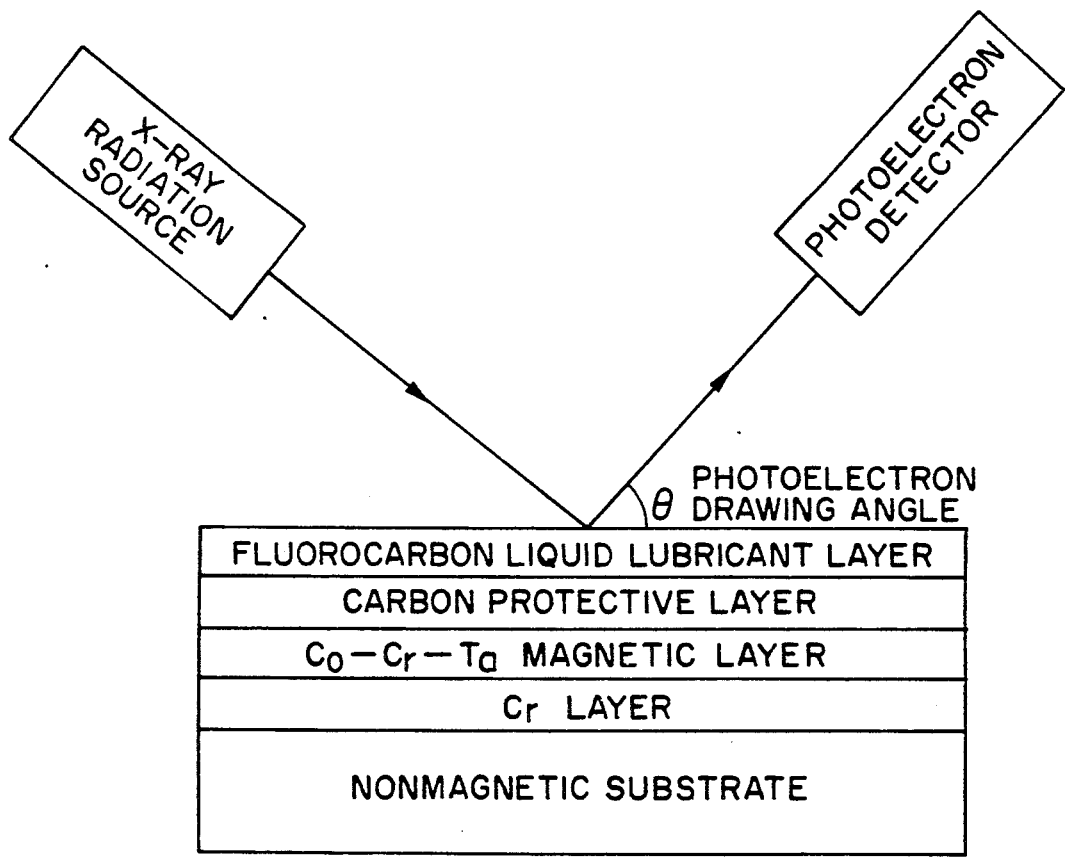
FIG. 8 is a diagram showing the physical relationship of the X-ray radiation source, the photoelectron drawing angle and the layers to one another.
Figure 9:
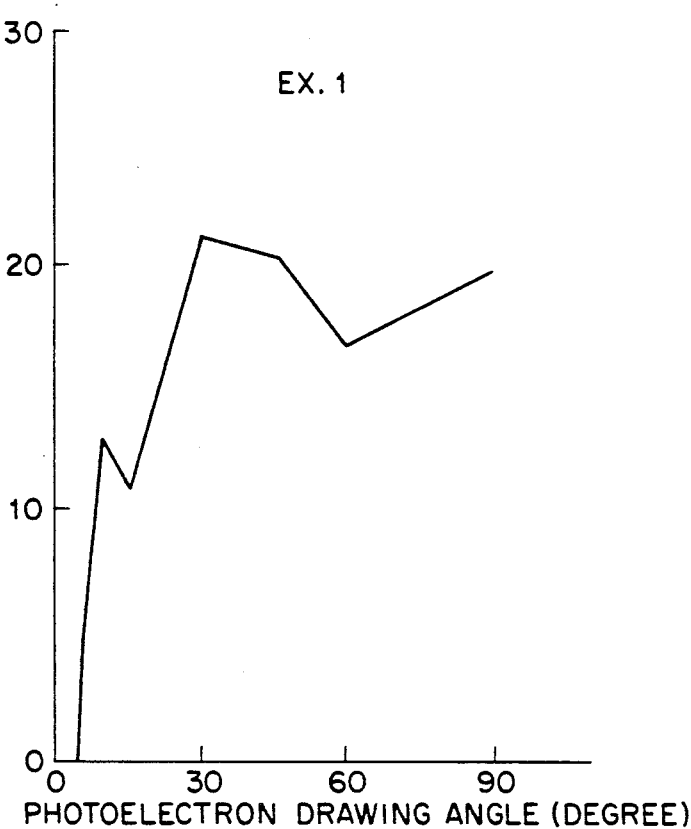
FIGS. 9-13 represent the series of graphs depicted in FIG. 1 which have been separated and are depicted in separate figures to ensure clarity.
Figure 10:
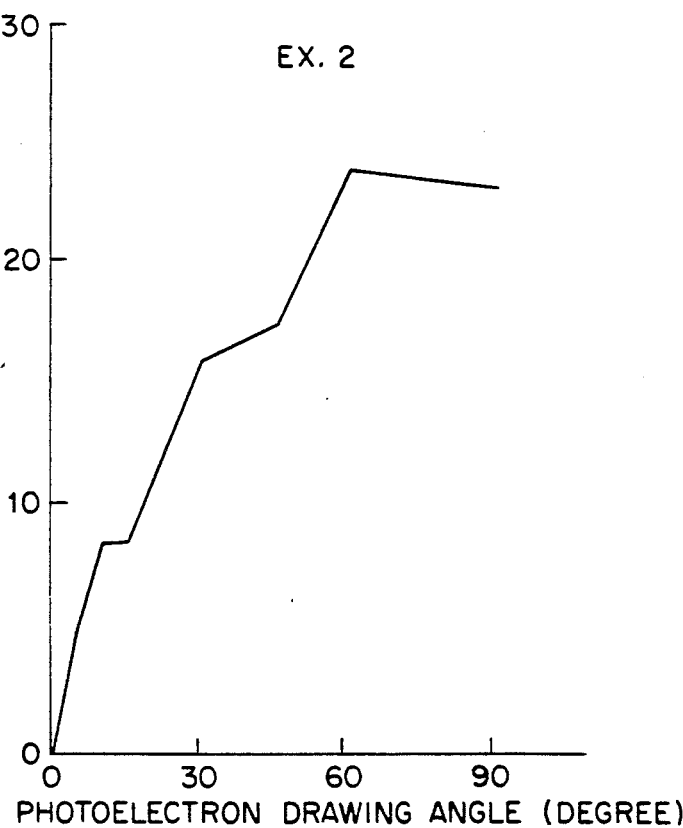
Figure 11:
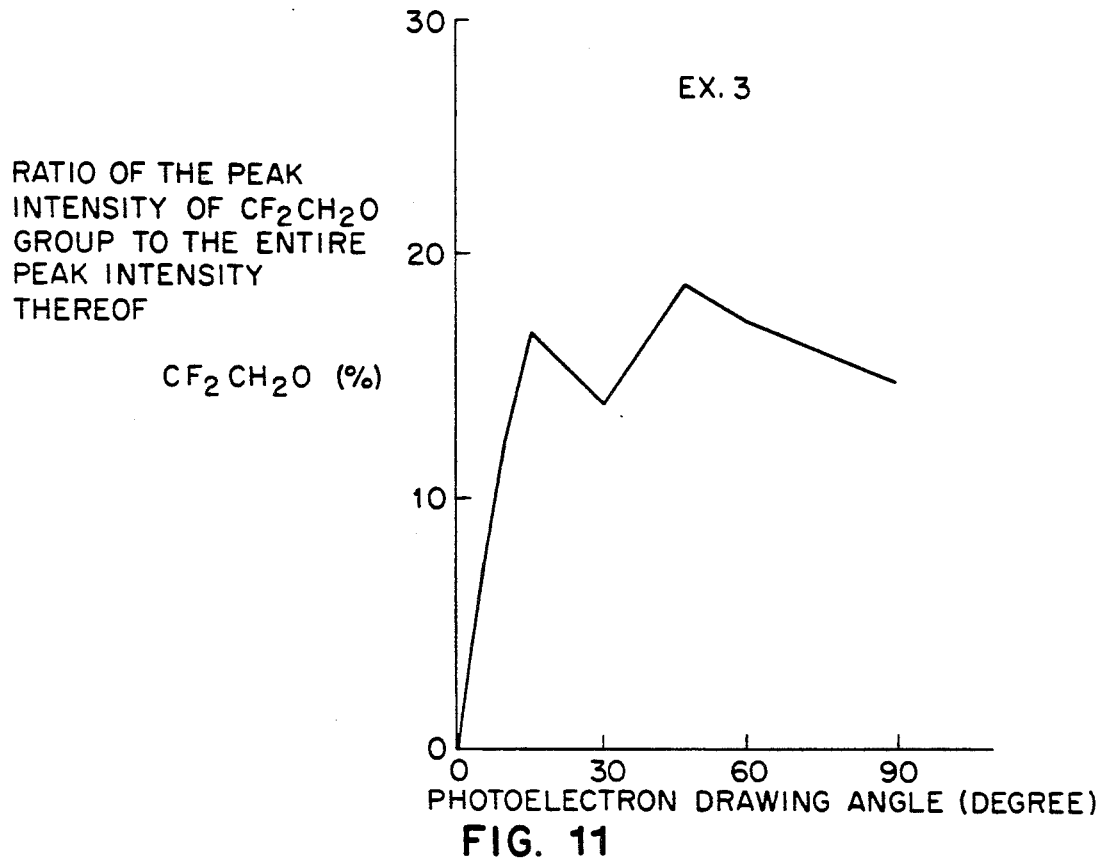
Figure 12:
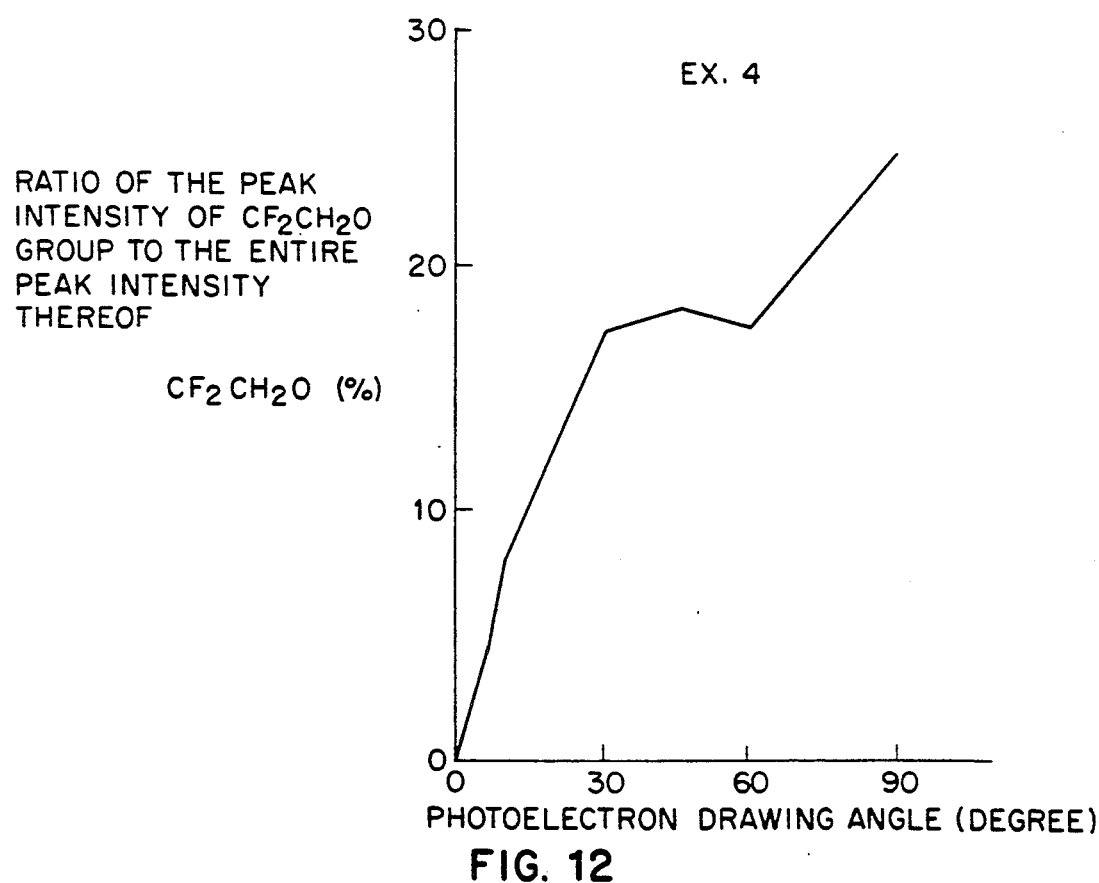
Figure 13:
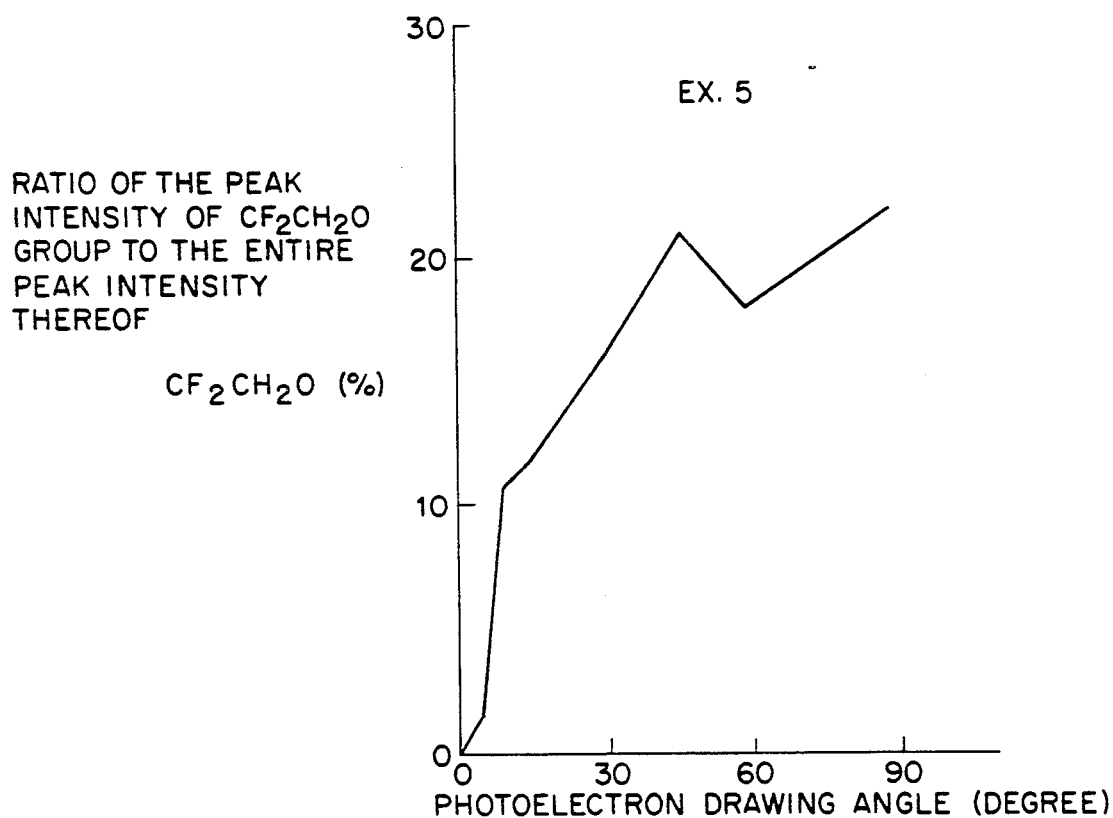
Figure 14:
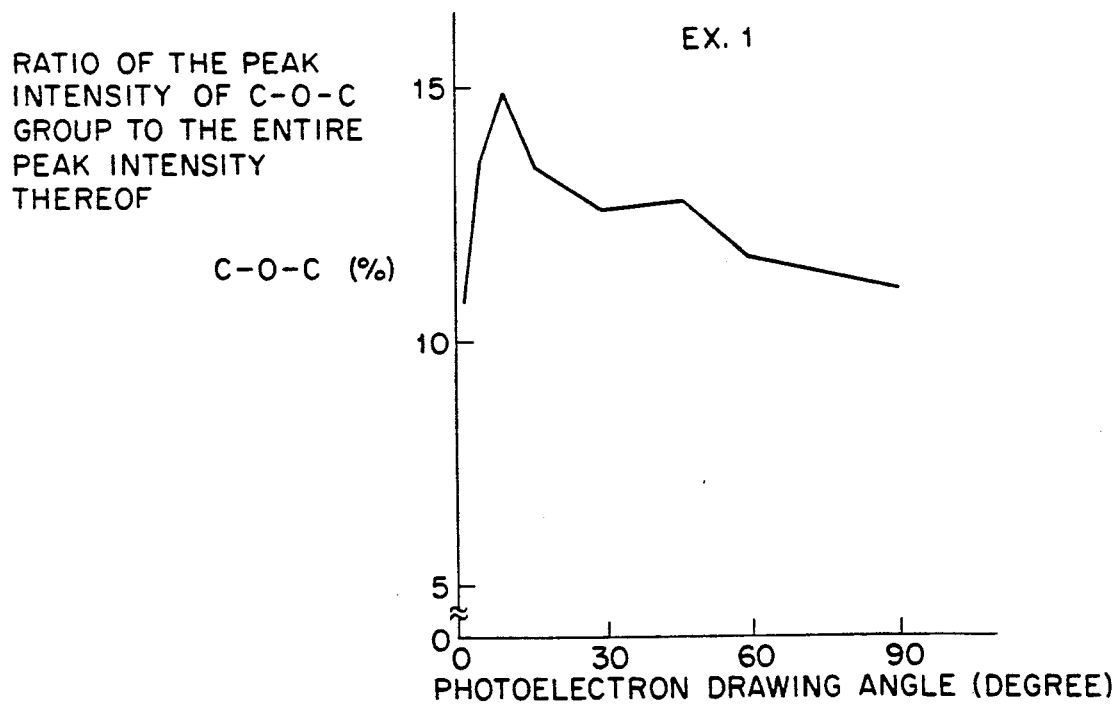
FIGS. 14-18 represent the series of graphs depicted in FIG. 2 which have been separated and are depicted in separate figures to ensure clarity.
Figure 15:
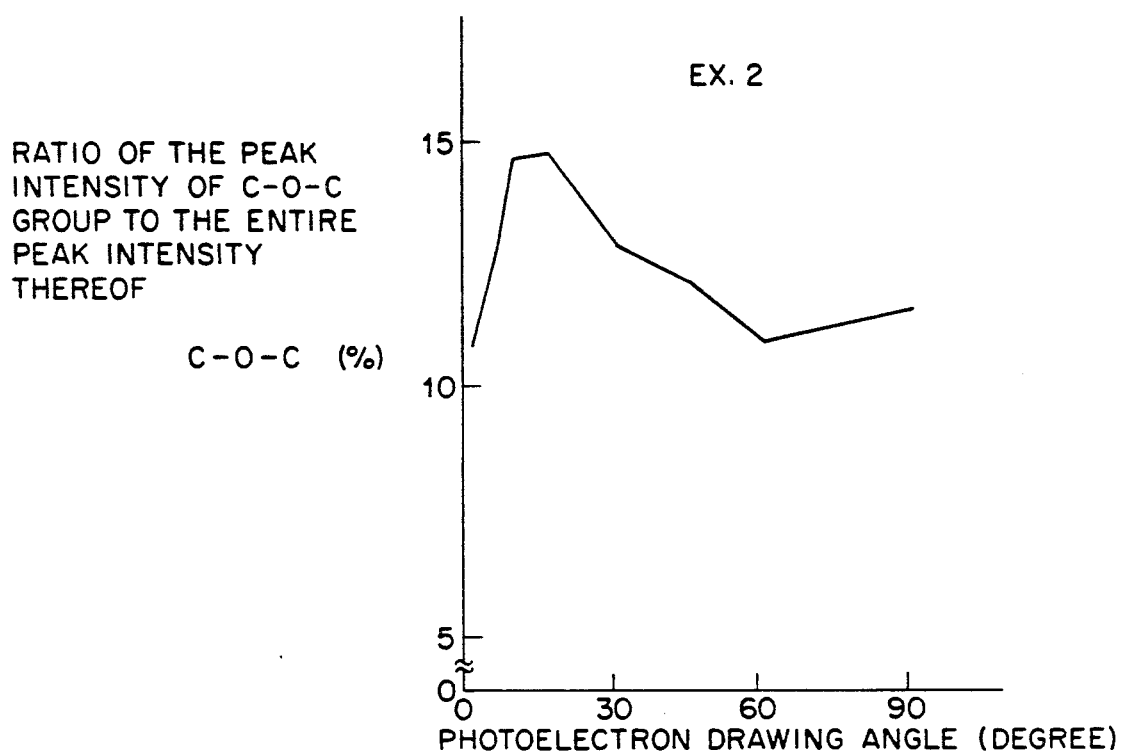
Figure 16:
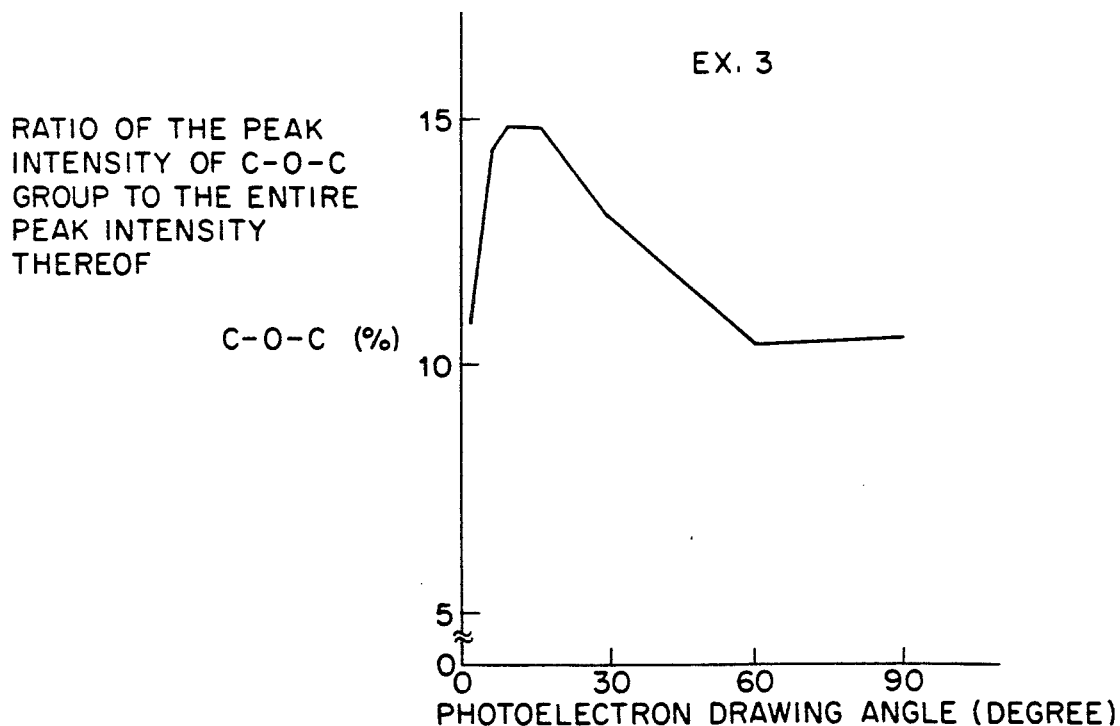
Figure 17:
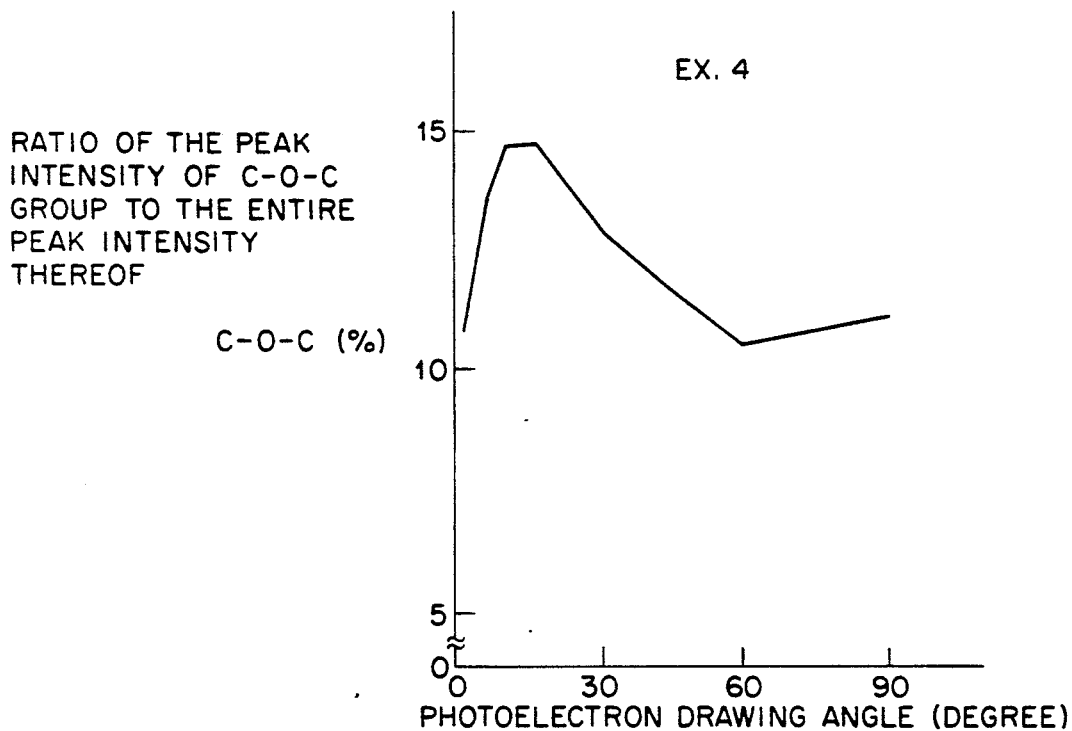
Figure 18:
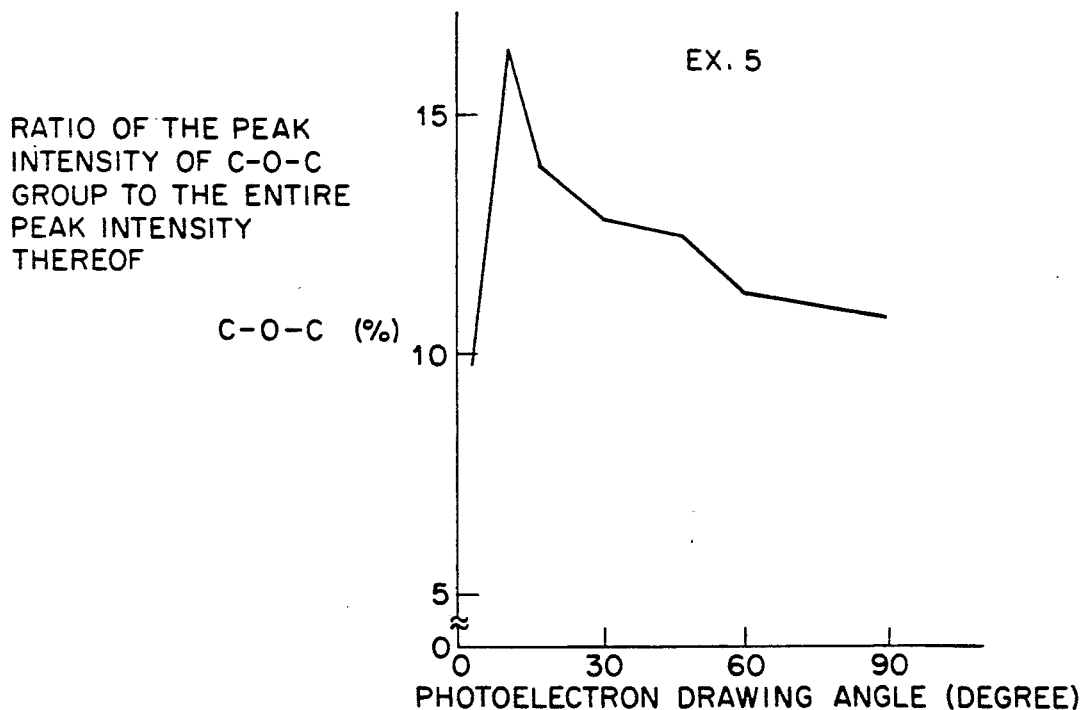

The first step in the method is to expose the lubricant molecules to a radiation source for X-ray photoelectron spectroscopy (ESCA) while varying the photoelectron drawing angle as depicted in FIG. 8. Since the magnitude of the drawing angle is related to the depth to which the lubricant molecules are exposed to the radiation source, a smaller drawing angle will result in the excitation of only those electrons on or near the surface of the lubricant layer.

Therefore, if the peak intensity of the polar group is extremely low at a small photoelectron drawing angle, the polar groups are oriented to the protective layer side, except for a few polar groups present on the surface side of the lubricant layer. On the other hand, if the peak intensity of the main chain portion is at its maximum at a small photoelectron drawing angle, the main chain portions are oriented to the surface side of the lubricant layer.

Thus, by varying the photoelectron drawing angle, and obtaining the ratios of the peak intensities of the polar group at the respective angles to the entire peak intensity of the polar group and the ratios of the peak intensities of the main chain portion at the respective angles to the entire peak intensity of the main chain portion, it is possible to determine the orientation of the polar group and main chain portions of the lubricant molecules in the lubricant layer.

A high quality lubricant layer, composed of lubricant molecules having appropriately long main chain portions with polar groups at the end, oriented so that the polar groups are predominantly toward the protective layer, and the main chain portions are predominantly toward the surface side, results in bringing the lubricant layer into close contact with the protective layer and the smooth sliding of the magnetic head. For a fluorocarbon lubricant, FONBLIN AM 2001, the desirable orientation of the molecules in such a layer is reflected by the measurement of a polar group peak intensity at a 16 degree drawing angle which is less than 12% and at a 90 degree drawing angle which is less than 20%, of the entire peak intensity of the polar group. In this same layer, the main chain portions are oriented to the surface side of the lubricant layer so that the main chain peak intensity at a 10 degree drawing angle is at a maximum, and at a 16 degree drawing angle is less than 14% of the entire peak intensity level of the group.

The following example is submitted to illustrate but not limit the invention.

EXAMPLE

A nonmagnetic substrate was produced by forming an Ni-P alloy layer on the surface of an Al alloy sheet by electroless plating whereby a metal coating is formed through the immersion of the substance into a suitable bath containing a chemical reducing agent. A Cr layer having a film thickness of 600 Å, a Co—Cr—Ta magnetic layer having a film thickness of 500 Å, and a carbon protective layer having a film thickness of 250 Å, were serially formed on the nonmagnetic substrate by sputtering (substrate temperature=250° C., Ar gas pressure=10 mTorr). A fluorocarbon liquid lubricant molecule, FONBLIN AM 2001 (produced by Montefluos), was then applied to the carbon protective layer to produce five samples of the magnetic recording media (Examples 1 through 5).

Each of these magnetic recording media was analyzed by ESCA while the photoelectron drawing angle, $\theta$, was varied from 0° to 90° and the degree of the orientation of the molecules in the lubricant layer was examined. The lubricant molecule, FONBLIN AM 2001, contains an aromatic group as a polar group. It is impossible to identify a peak intensity corresponding to the aromatic group specifically by ESCA, however, since the peak of the aromatic group is contained in the peak of C—C and the peak of C—H, both of which are also present in the main chain portion. It was therefore necessary to examine the peak of the —CF$_2$CH$_2$O— group which connects the aromatic group and the end of the main chain portion of the molecule.

Figure 1:
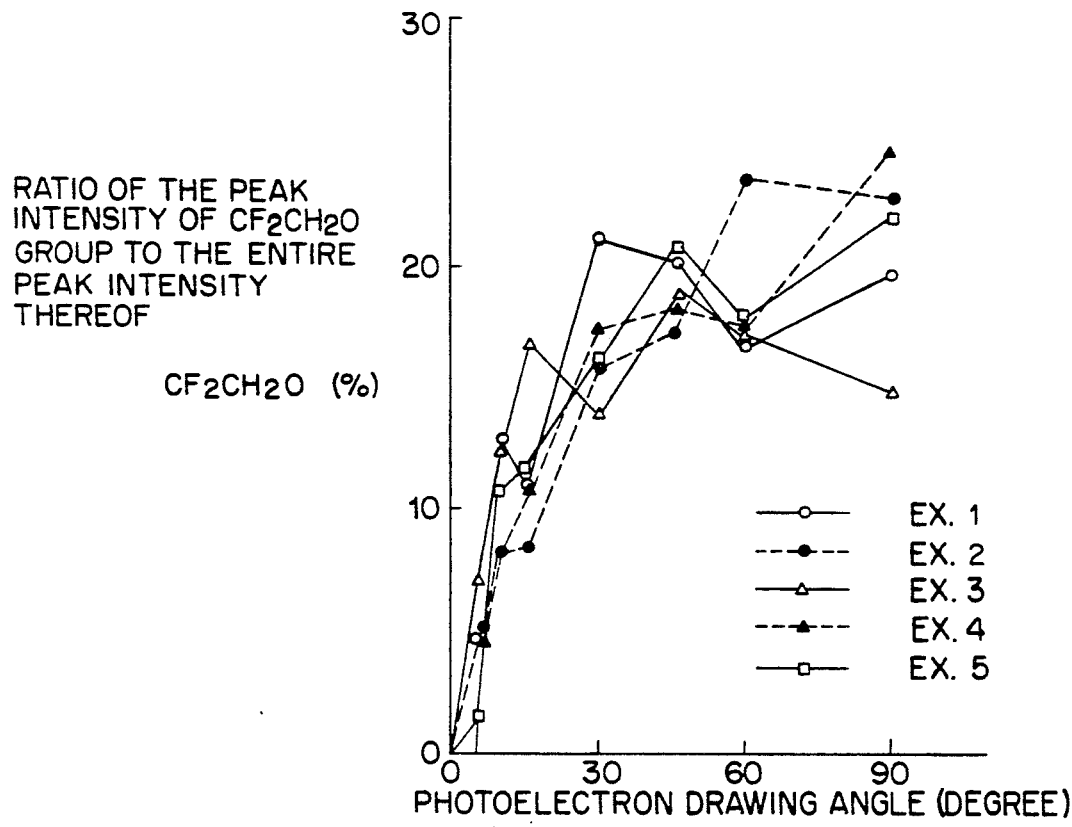
FIG. 1 is a graph showing the relationship between the photoelectron drawing angle and the ratio of the peak intensity of the $—CF_2CH_2O—$ group to the entire peak intensity of the group when a lubricant layer is analyzed by X-ray photoelectron spectroscopy.

FIG. 1 shows the ratio of the peak intensity of the —CF$_2$CH$_2$O— group at each angle to the entire peak intensity of the —CF$_2$CH$_2$O— group obtained by the analysis of the lubricant layer by ESCA with $\theta$ varied from 0° to 90°. Table 1 shows the ratios (%) of peak intensities of the —CF$_2$CH$_2$O— group at $\theta=16°$ and $\theta=90°$ to the entire peak intensity of —CF$_2$CH$_2$O— group.

Figure 2:
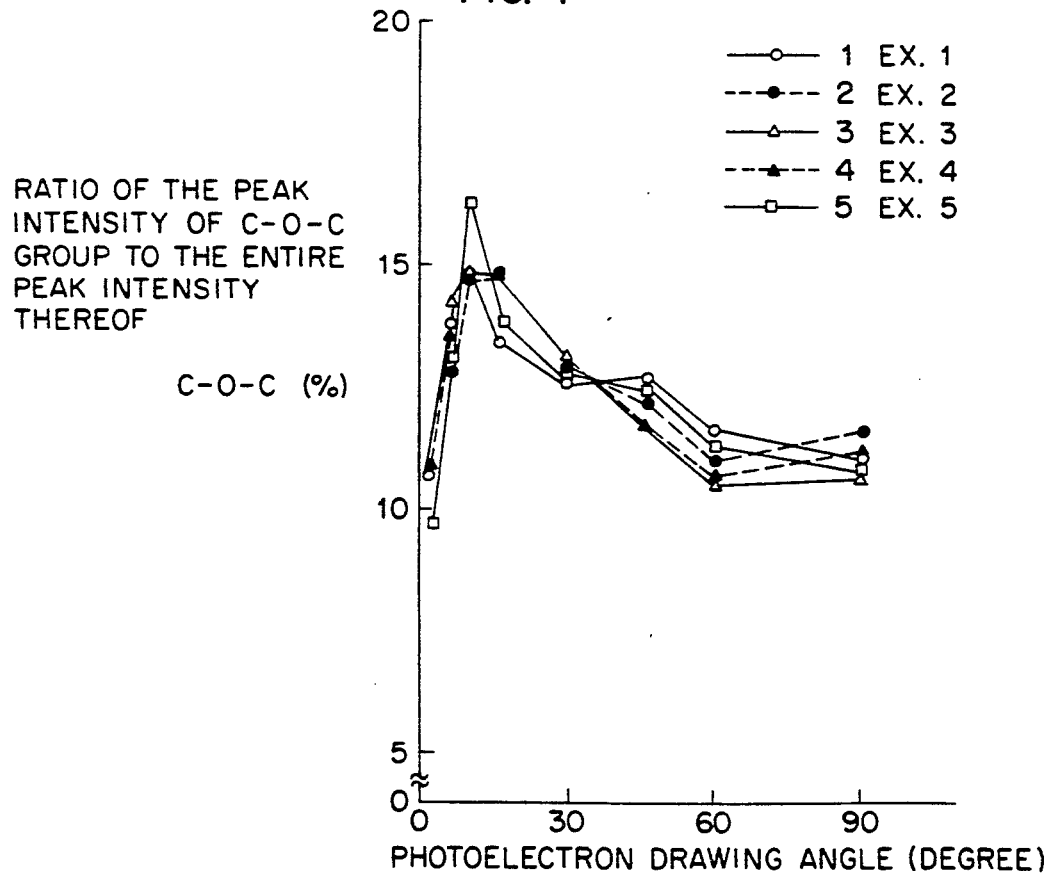
FIG. 2 is a graph showing the relationship between the photoelectron drawing angle and the ratio of the peak intensity of the C—O—C group to the entire peak intensity of the group when a lubricant layer is analyzed by X-ray photoelectron spectroscopy.
Figure 3:
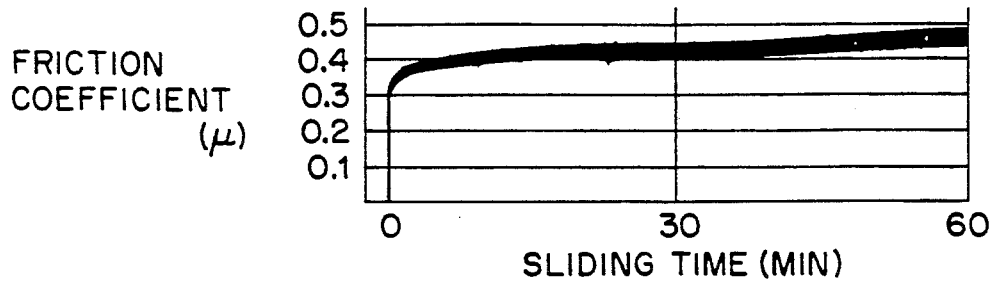
FIGS. 3 through 7 are graphs showing the results of the friction tests of magnetic recording media of Examples 1 through 5, respectively.
Figure 4:
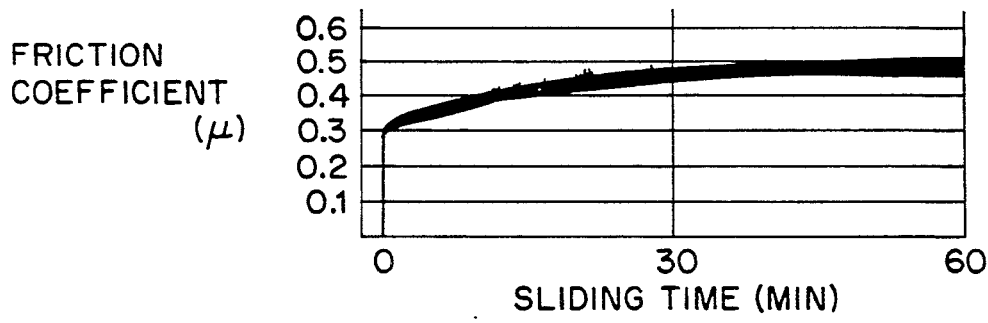
Figure 5:
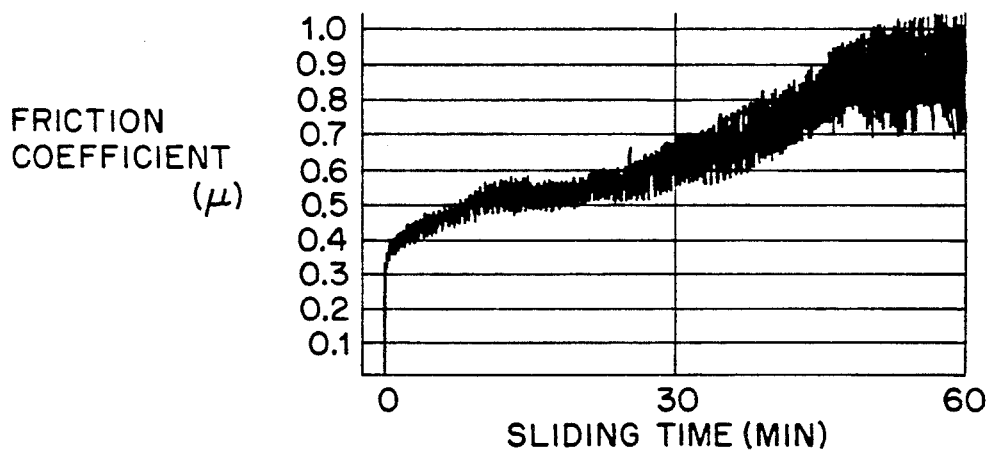
Figure 6:
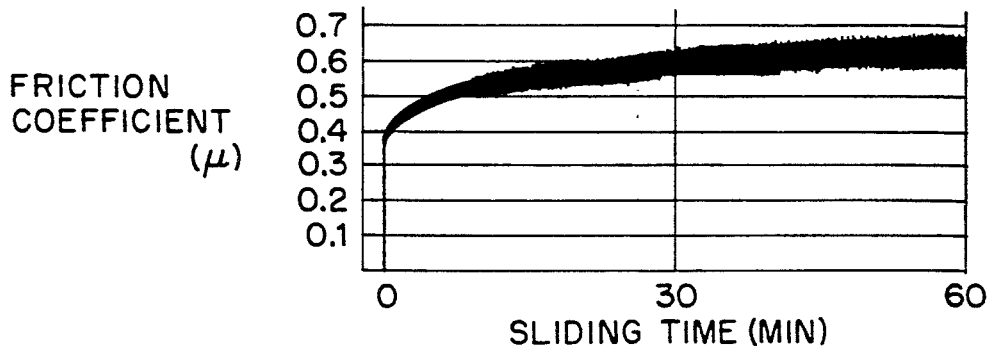
Figure 7:
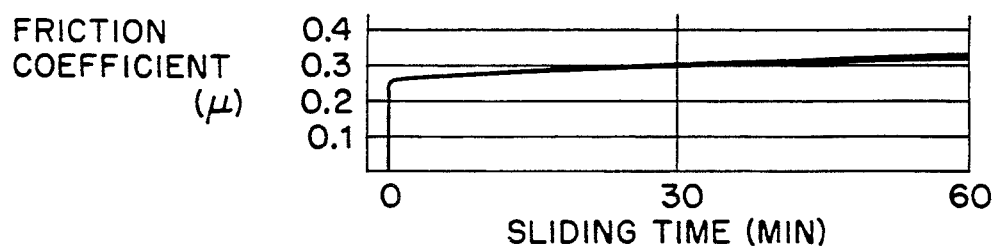

Since a fluorocarbon lubricant contains many oxygen atoms at the main chain portion, it is possible to examine the degree of orientation from the peak intensity of the C—O—C group. FIG. 2 shows the ratio of the peak intensity of the C—O—C group at each angle to the entire peak intensity of the C—O—C group obtained by the analysis of the lubricant layer by ESCA with $\theta$ varied from 0° to 90°. Table 1 shows the ratio (%) of peak intensities of the C—O—C group at $\theta=16°$ and the drawing angle $\theta$ at which the peak intensity of the C—O—C group is at its maximum.

The lubricating property of each of the magnetic recording media was evaluated by a friction test. As the test head for the friction test, an Al$_2$O$_3$-TiC head was used. The friction coefficient was measured when the magnetic head was brought into sliding contact with the surface of the magnetic recording medium which was rotating at 100 rpm on the circumference, 35 mm from the center. The results of the tests on Examples 1 through 5, are shown in FIGS. 3 through 7, respectively. The friction coefficient $\mu_{60}$ of each of the magnetic recording media obtained by sliding the magnetic head for 60 minutes in the friction test is also shown in Table 1.

TABLE 1

| | Degree of Orientation of Polar Groups | | Degree of Orientation of Main Chain Portions | | Lubricating Property $\mu_{60}$ |
|---|---|---|---|---|---|
| | $\theta$ 16° (%) | $\theta$ 90° (%) | $\theta$ 16° (%) | $\theta$ Having Maximum Peak Intensity | |
| Ex. 1 | 10.7 | 19.3 | 13.3 | 10° | 0.45 |
| Ex. 2 | 8.3 | 22.5 | 14.7 | 16° | 0.48 |
| Ex. 3 | 16.7 | 14.7 | 14.7 | 16° | 0.9 |
| Ex. 4 | 10.8 | 24.3 | 14.7 | 10° | 0.62 |
| Ex. 5 | 11.6 | 21.8 | 13.1 | 10° | 0.32 |

From FIGS. 3 through 7 and the values $\mu_{60}$ in Table 1, it is clear that the lubricating property of the recording medium of Example 5 is excellent while that of the recording medium of Example 3 is poor. The recording media of Examples 1 and 2 are essentially without any problem in practical use while the recording medium of Example 4 has a slight problem in practical use.

In Table 1, the degree of orientation of the polar groups was judged to be good when it was not more than 12% at $\theta=16°$ and not less than 20% at $\theta=90°$, and the degree of orientation of the main chain groups was judged to be good when it was at its maximum at $\theta=10°$ and it was not more than 14% at $\theta=16°$. The total evaluation of the degree of orientation in the lubricant molecules in each magnetic recording medium is shown in Table 2 together with the judgment of the lubricating property.

TABLE 2

| | Degree of Orientation In the Lubricant | | | Lubricating Property |
|---|---|---|---|---|
| | Polar Group | Main Chain Portion | Total | |
| Ex. 1 | x | ○ | Δ | ○ |
| Ex. 2 | ○ | x | Δ | ○ |
| Ex. 3 | x | x | x | x |
| Ex. 4 | ○ | x | Δ | Δ |
| Ex. 5 | ○ | ○ | ○ | ⊚ |

In Table 2, ⊚ represents an excellent value, ○ represents a good value, Δ represents an unacceptable value and x represents a poor value. It is apparent from Table 2 that there exists a relationship between the degree of orientation in the lubricant molecules and the lubricating property of the magnetic recording medium. It is therefore possible to determine the quality of the lubricating property of the magnetic recording medium by comparing the degrees of orientation in the lubricant molecules with those found to be indicative of high quality lubricant layer.

The difference in the degree of the orientation in the lubricant molecules which constitute the lubricant layer on the surface of the magnetic recording media is considered to be caused chiefly by the following: the nonuniformity of the film quality and the surface roughness of the carbon protective layer which is ascribed to the nonuniformity of the sputtering conditions for forming the Cr layer, the Co—Cr—Ta magnetic layer and the carbon protective layer; the nonuniformity of the film thickness; and the nonuniformity of the gas ingredient for the sputtering atmosphere. The method of the invention provides a ready tool to assess the impact of these various factors and makes possible a study of how to control them to achieve a consistently high quality product.

Having set forth the general nature and specific embodiments of the present invention, the true scope is now particularly pointed out in the appended claims.

We claim:

1. A method for determining the quality of a lubricant layer, formed from lubricant molecules having main chain and polar group portions, on a surface of a magnetic recording medium having a protective layer which comprises:
    (a) exposing the lubricant layer to a radiation source for X-ray photoelectron spectroscopy while varying the photoelectron drawing angle;
    (b) determining the numbers of emitted electrons at varying drawing angles corresponding to the main chain and polar group portions and the drawing angle which the number of emitted electrons corresponding to the main chain portions is at its maximum; and
    (c) assessing the degree of orientation of the polar group portion towards the protective layer from the information collected in step (b), wherein a high degree of orientation towards the protective layer is indicative of a high quality lubricant layer.

2. A method according to claim 1, wherein the lubricant layer is formed on a magnetic layer which is formed on a nonmagnetic substrate.

3. A method according to claim 2, wherein the magnetic recording medium comprises a carbon protective layer disposed between the magnetic layer and the lubricant layer.

4. A method according to claim 3, wherein the number of electrons emitted corresponding to the polar group portion at a 16 degree drawing angle and at a 90 degree drawing angle are compared to the entire peak intensity of the group and wherein, a 16 degree peak intensity which is less than 12%, and a 90 degree peak intensity which is less are indicative of a high quality lubricant layer in which the polar groups of the lubricant molecules are oriented to the side of the lubricant layer in contact with the carbon protective layer.

5. A method according to claim 4, wherein the number of electrons emitted corresponding to the main chain portion at a 16 degree drawing angle is compared to the entire peak intensity of the group and wherein, a 16 degree peak intensity which is less than 14% of the entire peak intensity of the group is indicative of a high quality lubricant layer in which the main chain portions of the lubricant molecules are oriented to the surface side of the lubricant layer.

6. A method according to claim 5, wherein a determination that the drawing angle at which the number of electrons emitted from the main chain portion of the lubricant molecule is at a maximum at about 10 degrees is indicative of a high quality lubricant layer in which the main chain portions of the lubricant molecules are oriented to the surface side of the lubricant layer.

* * * * *

UNITED STATES PATENT AND TRADEMARK OFFICE
CERTIFICATE OF CORRECTION

PATENT NO. : 5,144,134
DATED : September 1, 1992
INVENTOR(S) : Onodera et al.

It is certified that error appears in the above-identified patent and that said Letters Patent is hereby corrected as shown below:

Column 6, line 21, "less" should read --less than 20%, of the entire peak intensity of the polar group,--.

Signed and Sealed this

Ninth Day of November, 1993

Attest:

BRUCE LEHMAN

Attesting Officer

Commissioner of Patents and Trademarks